(12) United States Patent
Kieper et al.

(10) Patent No.: US 8,249,693 B2
(45) Date of Patent: *Aug. 21, 2012

(54) GAMMA GUIDED STEREOTACTIC LOCALIZATION SYSTEM

(75) Inventors: Douglas A. Kieper, Seattle, WA (US); Benjamin Lawrence Welch, Hampton, VA (US); Lee Holland Fairchild, Poquoson, VA (US)

(73) Assignee: Dilon Technologies, Inc., Newport News, VA (US)

( * ) Notice: Subject to any disclaimer, the term of this patent is extended or adjusted under 35 U.S.C. 154(b) by 1070 days.

This patent is subject to a terminal disclaimer.

(21) Appl. No.: 12/218,602

(22) Filed: Jul. 16, 2008

(65) Prior Publication Data

US 2010/0016865 A1   Jan. 21, 2010

(51) Int. Cl.
*A61B 6/00* (2006.01)
(52) U.S. Cl. ......... 600/436; 600/407; 600/425; 600/426
(58) Field of Classification Search .................. 600/407, 600/425, 426, 436
See application file for complete search history.

(56) References Cited

U.S. PATENT DOCUMENTS

| | | | | |
|---|---|---|---|---|
| 4,250,392 A * | 2/1981 | Leask et al. | ................ | 250/505.1 |
| 5,855,554 A * | 1/1999 | Schneider et al. | ............ | 600/407 |
| 5,961,457 A | 10/1999 | Raylman et al. | | |
| 6,229,145 B1 | 5/2001 | Weinberg | | |
| 6,271,525 B1 | 8/2001 | Majewski et al. | | |
| 6,389,098 B1 | 5/2002 | Keppel et al. | | |
| 6,424,693 B1 | 7/2002 | Weisenberger | | |
| 6,927,406 B2 * | 8/2005 | Zyromski | ................. | 250/496.1 |

OTHER PUBLICATIONS

Welch et al. "Quality Assurance Procedure for a Gamma Guided Stereotactic Breast Biopsy System." Physica Medica. pp. 102-105, 2006.*

* cited by examiner

*Primary Examiner* — Tse Chen
*Assistant Examiner* — Mark Remaly (57) ABSTRACT

A stereotactic gamma-guided localization system for imaging a suspected cancer and guiding a physician in the removal of tissue samples for biopsy. The gamma-guided localization system includes a three step procedure including localization, correlation, and verification. The localization system includes a gamma camera with a set of slant-hole collimators for producing stereo images of a region of interest. A positioning system including a fiducial marker is placed adjacent to the object to be imaged and held rigidly in place to provide correlation of the location of the region of interest relative to the fiducial marker. A gamma emitting marker is then positioned at the calculated location of the region of interest and imaged to verify that that the calculated position corresponds to the actual location. The positioning system can then be used to accurately position and support any other hardware that needs to be positioned at the region of interest.

12 Claims, 5 Drawing Sheets

Fig. 10 - Images of sources at various heights.

Fig. 11 - Graph of the two images of the point sources located at various heights which was used to determine the separations.

Fig. 12 - Graph of the separation of the two images of the source versus the actual height. The slope of this line serves as the calibration of the slant hole pair.

GAMMA GUIDED STEREOTACTIC LOCALIZATION SYSTEM

FIELD OF THE INVENTION

This invention relates to imaging of suspected cancer and specifically to a gamma imaging system used to guide a physician in the removal of tissue samples for biopsy.

BACKGROUND OF THE INVENTION

Mammographic imaging is well established as the primary screening modality for breast cancer. A suspicious finding on a mammographic examination may lead to imaging with another modality to further investigate the suspicious finding and ultimately to a biopsy being performed to confirm that cancer is or is not present. The other modalities may include a diagnostic mammogram, an ultrasound (US) examination, a magnetic resonance imaging (MRI) procedure, or a nuclear medicine procedure (known as scintimammography). Depending on the nature of the finding and the imaging system with which it was found, the surgeon or radiologist may be guided in the removal of tissue for pathological examination by one of these imaging systems. Breast biopsy systems have been produced and marketed which rely on x-ray guidance, US guidance, and MRI guidance.

Mammograms are x-rays that image tissue densities, not cancer activity. It can be difficult to identify cancerous lesions using mammography, especially when patients have dense breast tissue, multiple suspicious lesions or clusters of microcalcifications, palpable lesions not detected by mammography or ultrasound, post-surgical or post-therapeutic mass, implants, or have been taking Hormone Replacement Therapy.

MRI has shown usefulness as a next-step imaging modality for difficult-to-diagnose cases. Much like x-ray mammography, breast MRI relies on anatomical or structural information, but provides much more detailed images. It is limited, however, by its highly variable specificity, which can range from below 37% to 97%. Combined with its high sensitivity, it is expensive, may require multiple days to complete, and produces a high false positive rate.

Ultrasound is also commonly utilized as a next-step after a questionable mammogram and is good at determining if a suspect mass is solid or fluid-filled. However, ultrasound demonstrates a low specificity rate that can produce misleading results and indicate biopsy where one may not be needed.

Although biopsy systems employing x-ray, ultrasound, and MRI modalities exist, there remains a need for achieving further accuracy in determining the location of potentially cancerous lesions and for the accurate guidance of biopsy systems to the cancerous lesions.

SUMMARY OF THE INVENTION

The invention is a stereotactic gamma-guided localization technique for imaging a suspected cancer and guiding a physician in the removal of tissue samples for biopsy. The gamma-guided localization technique includes a three step procedure including localization, correlation, and verification. The localization system includes a gamma camera with a set of slant-hole collimators for producing stereo images of a region of interest. A positioning system including a fiducial marker is placed adjacent to the object to be imaged and held rigidly in place. The positioning system provides correlation of the location of the region of interest relative to the fiducial marker. A gamma emitting marker is then positioned at the calculated location of the region of interest and imaged to verify that that the calculated position corresponds to the actual location. The positioning system can then be used to accurately position and support any other hardware that needs to be positioned at the region of interest, by measurements from the fiducial marker.

OBJECT OF THE INVENTION

It is therefore an object of the present invention to provide a stereotactic localization system that can provide valuable information for determining extent of a primary lesion, detecting occult secondary lesions, and evaluating the axillary region for node status in breast cancer patients.

It is an object of the present invention to provide a functional procedure that images cancer activity rather than imaging tissue structure such as in prior art imaging techniques.

It is a further object of the present invention to provide a complementary diagnostic procedure to mammography that has greater sensitivity and specificity in identifying cancerous lesions.

It is another object of the present invention to provide a technique that produces two gamma camera images of an object at different angles to determine the three dimensional location of a region of interest in the object relative to the camera system.

A further object of the present invention is to provide a positioning system for placing a biopsy needle accurately at an identified region of interest.

Another object of the present invention is to provide a biopsy marker that includes a small radioactive source that can be imaged by a gamma camera.

These and other objects and advantages of the present invention will be better understood by reading the following description along with reference to the drawings.

TABLE OF NOMENCLATURE

The following is a listing of part numbers used in the drawings along with a brief description:
20 gamma guided stereotactic localization system
22 stereo imaging system
23 gamma camera
24 gamma camera crystal
26 first or left side slant-hole collimator
28 second or right side slant-hole collimator
30 collimator set
32 object to be imaged or body part
34 direction of travel of collimator set
36 positioning system
38 grid localization system or grid localization plate
40 fiducial source or marker
42 region of interest
44 biopsy needle guide
46 gamma emitting marker source or obturator
48 camera viewing lines
50 grid support or shield
52 cavity
54 grid
56 grid opening
58 row in grid
60 column in grid
62 cassette
64 inner tube
66 outer cannula
70 gamma guided stereotactic localization system
72 parallel hole collimator
74 line or seam where two slant-hole collimators are joined
76 biopsy needle
78 overlap region
$\Theta_1$ stereotactic viewing angle of left slant-hole collimator
$\Theta_2$ stereotactic viewing angle of right slant-hole collimator

DETAILED DESCRIPTION OF THE INVENTION

The present invention provides a gamma guided stereotactic localization system for accurately locating and guiding biopsy equipment to cancerous lesions. The gamma guided stereotactic localization system of the present invention is a functional or molecular breast imaging procedure that captures the metabolic activity of breast lesions through radiotracer uptake. A small amount of tracing agent is delivered to a patient, and in turn is absorbed by all cells in the body. The tracing agent emits invisible gamma rays, which are detected by a gamma camera and translated into a digital image of the breast. Due to the higher metabolic activity of cancerous cells, these cells absorb a greater amount of the tracing agent and are revealed as "hot spots." This molecular breast imaging technique can help doctors more reliably differentiate cancerous from non-cancerous cells. While other adjunct modalities, such as MRI and ultrasound, image the physical structure of the breast, the gamma guided stereotactic system of the present invention captures the cellular functioning of the breast tissue.

Stereotactic localization uses two images of an object taken at different angles to determine the three dimensional location of a region-of-interest in that object, relative to the imaging system coordinates. It is desirable to have a gamma-guided localization system for use in the gamma imaging of suspected cancer to guide a physician in the removal of tissue samples for biopsy.

It is also desirable to correlate the location of the region relative to the camera with the location of the region in the object and to provide a positioning system that can be used to support and accurately position other hardware in the vicinity of the object. Once the location is correlated with the object, it can be used, for example, for positioning a needle in a suspected tumor to collect a tissue sample for biopsy.

In an effort to reduce that chance for error in this localization system a means to verify that the calculated location does indeed correspond to the location of the lesion is also desirable. This requires a marker to be placed in the object and the imaging system used to image this marker at that location. That image can then be compared with the image of the region of interest. In order to be imaged by the gamma camera, these markers must be radioactive and the marker must be seen in the image of the object. The current invention satisfies these requirements.

Figure 1:
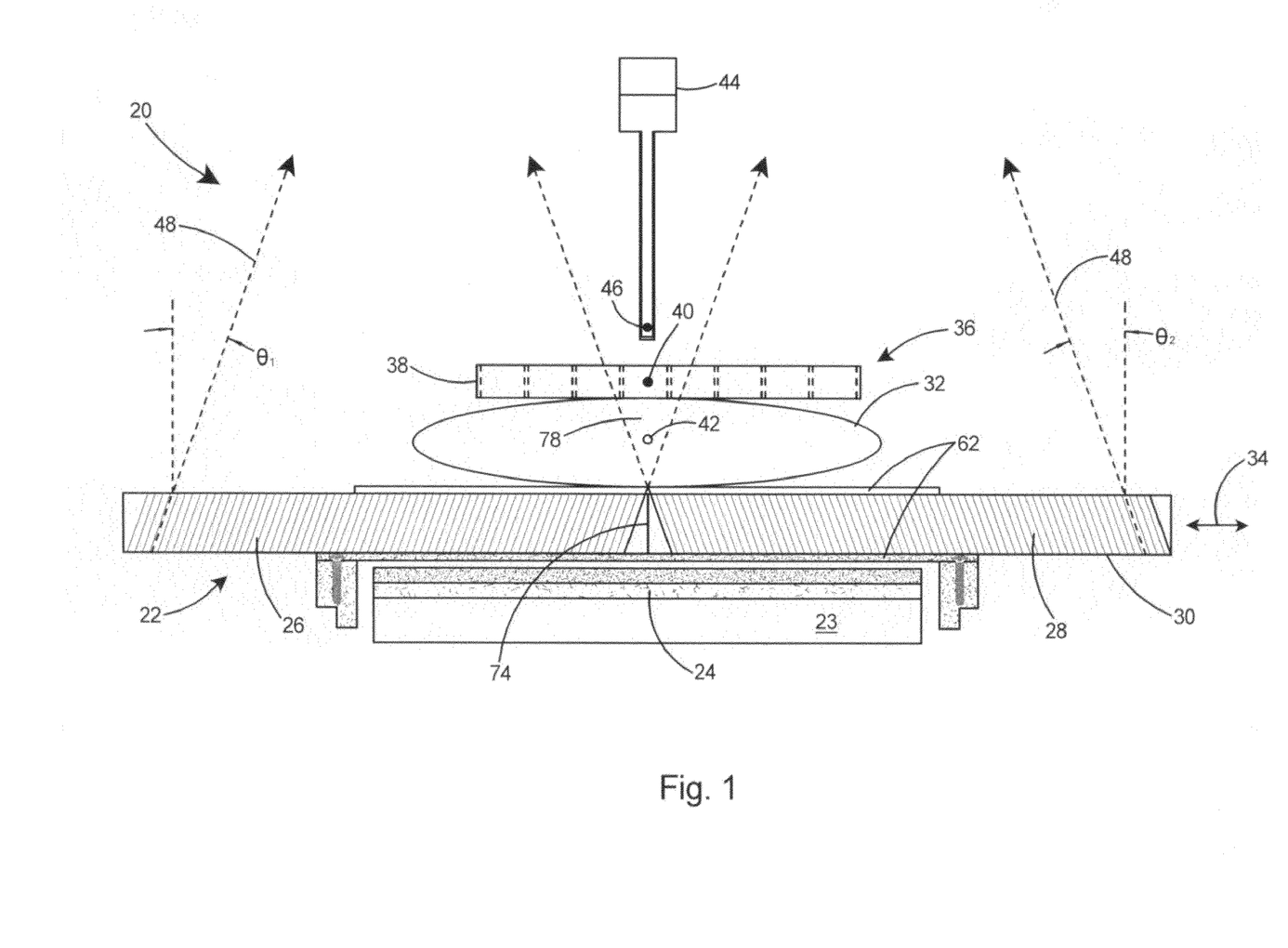
FIG. 1 is a conceptual front view of a preferred embodiment of a gamma guided stereotactic localization system according to the present invention including a gamma camera crystal, a stereo imaging system including a set of oppositely viewing slant-hole collimators, and a grid localization system with a fiducial marker source.

With reference to FIG. 1 there is shown a preferred embodiment of the present invention, a gamma guided stereotactic localization system 20. The gamma guided stereotactic localization system 20 includes a stereo imaging system 22 composed of a gamma camera 23 including a gamma camera crystal 24 and a set of oppositely viewing slant-hole collimators. A first or left side slant-hole collimator 26 and a second or right side slant-hole collimator 28 are coplanar with each other and joined at their ends form a side-by-side collimator set 30 that is movable with respect to the gamma camera crystal 24 and the body part or object 32 to be imaged. The collimator set 30 is movable left to right in FIG. 1 as shown by directional arrow 34. A positioning system 36 includes a grid localization system or plate 38 that is rigidly mounted above the object 32 to be imaged. A radioactive fiducial source 40 that can be imaged by the stereo imaging system 22 is accurately mounted in the positioning system 36. The stereo imaging system 22 is used to accurately identify a region-of-interest 42, such as a suspected cancerous lesion, in the object 32 to be imaged. The positioning system 36 is placed adjacent to the object 32 to be imaged and is used to support and accurately position other hardware, such as the biopsy needle guide 44 shown in FIG. 1, in close proximity to the object 32. A marker source 46, shown in the end of the biopsy needle guide 44, can be inserted into the object 32 at the calculated location of the region of interest 42 or lesion and used to verify that the calculated location is the actual location of the lesion. As shown by the angles of the conceptual camera viewing lines 48 in FIG. 1, the stereotactic viewing angles $\Theta_1$ and $\Theta_2$ are at +/−20 degrees with respect to a line perpendicular to the face of the gamma camera crystal 24. Left side slant-hole collimator 26 therefore views at a 20 degree angle to the right and right side slant-hole collimator 28 views at a 20 degree angle to the left.

The stereotactic gamma-guided localization method of the present invention involves three steps including localization, correlation, and verification. As shown in FIG. 1, the localization system includes a gamma camera having a gamma crystal 24 with a set of slant-hole collimators 26 and 28 that serve as the stereo viewing system. The positioning system 36 includes a grid localization system 38 with a fiducial source 40 therein and is placed adjacent to the object 32 to be imaged and held rigidly in place. The verification system includes a gamma emitting marker 46 that can then be placed by a biopsy needle guide 44 or similar tool at the calculated location of the region of interest 42 and imaged by the stereo imaging system 22 to verify that the inserted marker 46 coincides with the region of interest 42.

The location of the fiducial source 40 relative to the stereo imaging system 22 is calculated from the gamma camera images. The location of the region-of-interest 42 relative to the stereo imaging system 22 is then calculated to locate the region-of-interest 42 relative to the fiducial source 40. The positioning system 36 can then be used to accurately position and support any other hardware, such as the biopsy needle guide 44 shown in FIG. 1, which needs to be positioned at the region of interest 42, by measurements from the fiducial source 40. The marker source 46 is then be used to verify that the calculated location of the region of interest 42 corresponds to the actual location.

The stereotactic gamma-guided localization method of the present invention involves three steps including localization, correlation, and verification. More specifically, the localization step includes 1) placing a positioning system adjacent to the object to be imaged, 2) taking a pair of stereo images of the object; 3) determining the region of interest in each of the stereo images, and 4) calculating the three dimensional (X, Y, and Z) location of the region of interest. Correlation includes 1) locating the fiducial marker in each of the images, 2) calculating the (X, Y and Z) location of the fiducial marker, 3) locating the region-of-interest relative to the fiducial marker within the positioning system, and 4) utilizing the positioning system to locate and support any other hardware that needs to be positioned at the region of interest. Verification includes 1) positioning a marker source at the calculated location of the region of interest, and 2) imaging with the stereo imaging system to verify that the calculated location indeed corresponds to the actual location.

Figure 2:
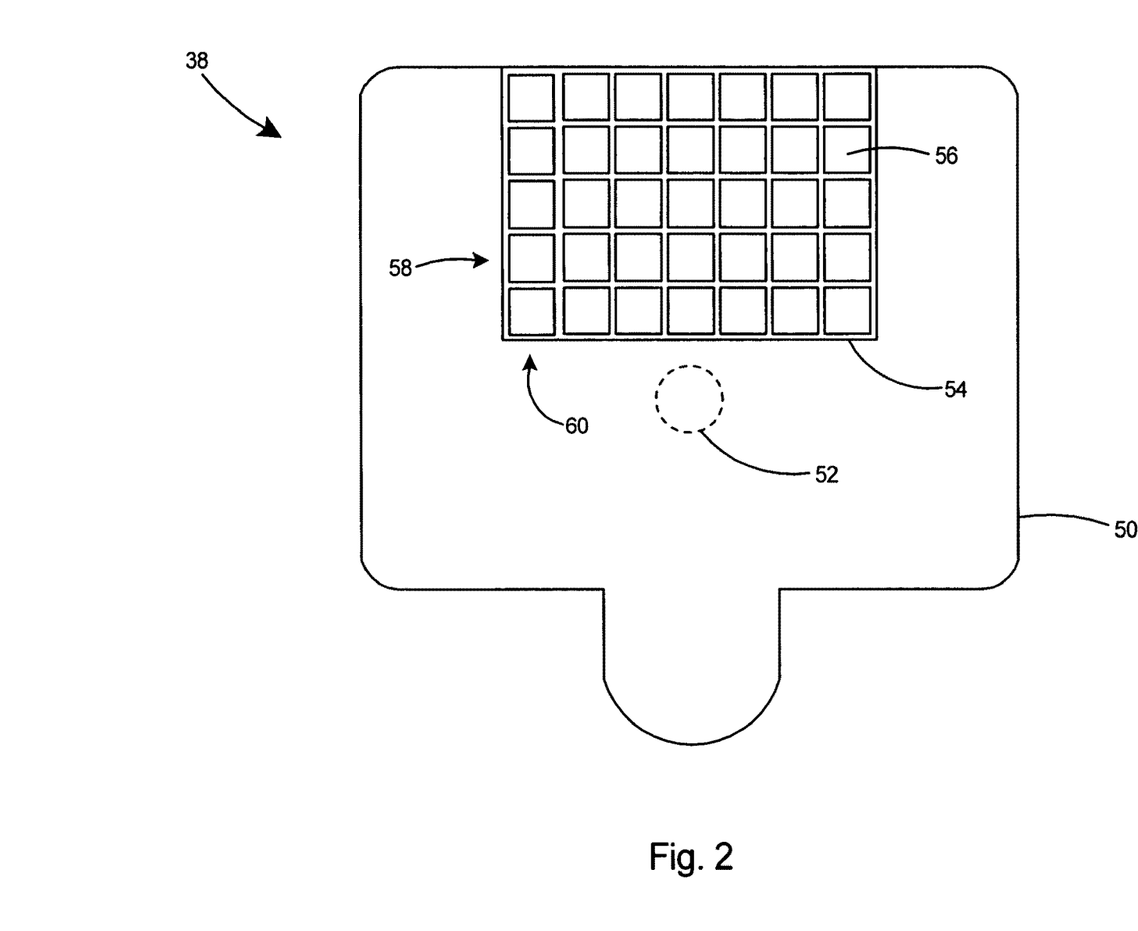
FIG. 2 is a top view of the grid localization system and fiducial marker source which form a portion of the gamma guided stereotactic localization system of FIG. 1.

With reference to FIG. 2 there is shown a top view of the grid localization system 38 that forms a portion of the gamma guided stereotactic localization system of the present invention. The grid localization system 38 includes a grid support or shield 50, a cavity 52 for accepting a fiducial source 40 therein, and a grid 54 with a plurality of grid openings 56 therein arranged in rows 58 and columns 60. The grid localization system 38 enables a qualified physician to perform a gamma guided breast biopsy using a standard breast biopsy needle kit. The grid shield 50 is typically used to immobilize the breast during an imaging procedure.

The grid localization system 38 is used to locate the area of the breast or other body part that is directly above the suspected lesion. The grid 54 will be correlated with the location of the lesion that has been determined during the localization procedure via the fiducial marker 40. The fiducial marker 40 is imaged at the same time as the lesion and the location of the lesion relative to the fiducial marker 40 is calculated. The grid localization system 38 will also serve to stabilize the biopsy needle system during the gamma guided breast biopsy procedure.

The fiducial marker 40 is typically inserted into a cavity 52 in the grid support 50. The fiducial marker 40 is mechanically registered to the grid system and is used to correlate the location of the suspected lesion as determined by the stereo imaging system 22 and the grid localization system 38. This allows the physician to determine the location of the suspected lesion by measurements from the grid localization system 38. Preferably, the fiducial marker 40 is a radioactive source of Co-57 inserted into the cavity 52 on the grid support 50. Preferably, the activity level of the fiducial marker 40 is sufficient to be seen simultaneously with the lesion in the imaged object 32 but low enough as to present no significant risk to the patient. The fiducial marker is typically refreshed annually or as indicated by an expiration date on the package.

The gamma guided stereotactic localization system 20 includes a cassette 62 (see FIG. 1) in which the collimator set 30 slides, and a computer including software having a biopsy protocol that is used to determine the three dimensional location of the lesion from the gamma camera images. The biopsy protocol takes the inputs from the stereo imaging system 22 and determines the three dimensional location of the lesion. Referring to FIG. 2, the biopsy protocol is also used to correlate the location of the lesion to the grid system 38 such that the biopsy needle 44 can be positioned at the appropriate location within the grid 54 and inserted into the object 32. The biopsy protocol will also allow images to be taken during the biopsy procedure, to determine that the biopsy needle 44 has been positioned correctly.

The gamma guided stereotactic localization system 20 of the present invention includes a marker validation procedure whereby the gamma emitting marker or obturator 46 (see FIG. 1) is used to determine that the incision in the object 32 has been made to the correct location. The marker 46, which will contain a radioactive source, will be inserted into the object after the incision is made and the object imaged with the gamma camera. The sliding collimator set 30 is positioned such that the gamma emitting source 46 can be imaged through both halves 26 and 28 of the slant-hole collimator. The two images of the gamma emitting marker 46 will appear in the location of the lesion if the incision has been made to the correct location, confirming that the biopsy is taken at the site of the suspected lesion 42.

Figure 3:
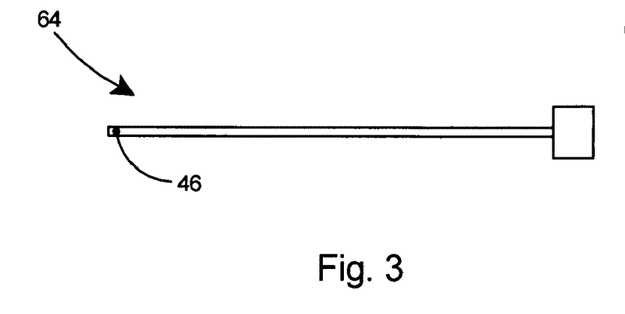
FIG. 3 is a side view of an inner tube that contains a gamma emitting marker source.
Figure 4:
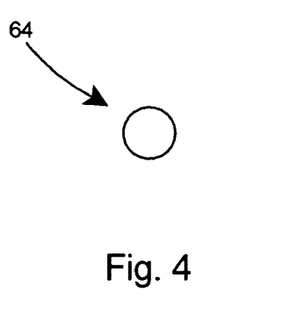
FIG. 4 is an end view of the inner tube depicted in FIG. 3.
Figure 5:
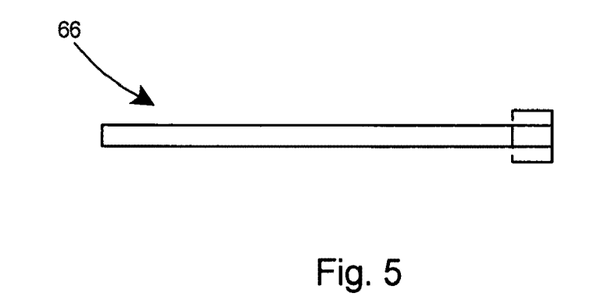
FIG. 5 is a side view of an outer cannula that will contain the inner tube of FIG. 3 and which will be in contact with the object to be imaged.
Figure 6:
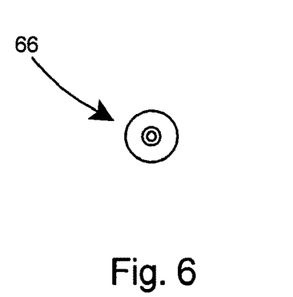
FIG. 6 is an end view of the outer cannula depicted in FIG. 5.
Figure 7:
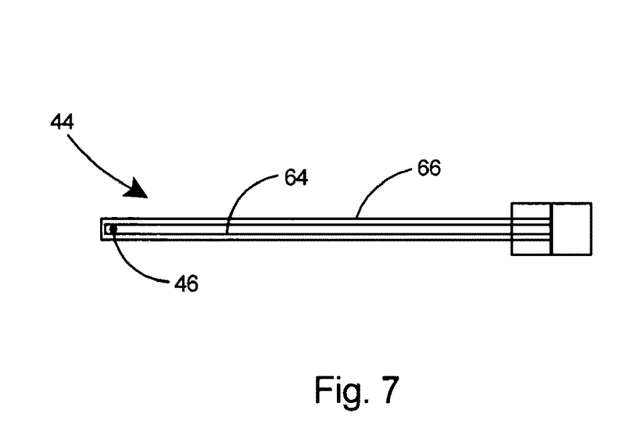
FIG. 7 is a phantom side view of a biopsy needle guide including an inner tube with a gamma emitting marker source and enclosed in an outer cannula.
Figure 8:
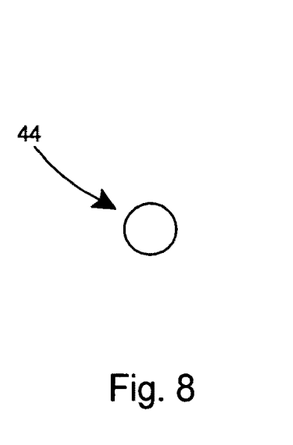
FIG. 8 is an end view of the biopsy needle guide of FIG. 7.

Referring to FIGS. 3-8, the gamma emitting marker has two parts including an inner tube 64 that contains the radioactive source 46 and an outer cannula 66 that will be in contact with body fluids in the object 32 to be imaged. The inner tube 64, as shown in FIGS. 3 and 4, is fitted into the outer cannula 66, depicted in FIGS. 5 and 6, to form the source holder or biopsy needle guide 44 with gamma emitting marker 46 as shown in FIGS. 7 and 8. The source holder 44 preferably contains a long half-life isotope such that it can be used for an extended period, and therefore used for a number of imaging and biopsy procedures. The half-life of the isotope is preferably of the order of a few months to a year. Preferably, the activity of the gamma emitting source 46 is such that it can be conveniently seen in the image, but not cause significant radiation exposure or overwhelm the image of the imaged object 32. This activity will depend on the gamma ray attenuation of the material used for the source holder 44 and the outer sleeve 66. Preferably the expected activities of the gamma emitting source 46 are in the range of 5-10 microcurie. For reference, the typical specific activity of the lesion is 2 microcurie/cc and that of the imaged object is 0.3 microcurie/cc.

The energy of the gamma rays emitted from the gamma emitting source 46 is preferably equal to or higher than the isotope used for the imaging of the object 32 through radiotracer uptake. The isotope used for imaging of the object 32 is preferably Tc-99m, with a gamma-ray energy of 140 keV. Examples of isotopes that have gamma ray emissions with energy greater than 140 keV and a relatively long half-life are Ce-139 with an energy of 166 keV and a half-life of 137.6 days, and Te-123m with an energy of 159 keV and a half-life of 120 days. These isotopes can be produced as solid materials and encapsulated into the source holder 44 and, as they have a greater gamma-ray energy than the isotope used for functional imaging, can be used as the gamma emitting source 46 within the obturator. For the gamma emitting source, it is preferable to use an isotope with a gamma ray transition at a slightly higher energy than the radiopharmaceutical used for the functional imaging. This allows dual energy windowing, and the markers are not in the scatter region of the spectrum which is typically at lower energy. This is because the scatter of the patient causes a large background at lower energy, which would require a higher activity in the source used for the marker. At higher energy, there is no scatter. This results in a lower activity source and a higher contrast image.

An alternative embodiment for the gamma emitting source 46 is a one piece design (not shown) that can be filled with a radioactive liquid. The radioactive liquid will have a short half-life and can therefore be safely discarded after an appropriate time, typically 10 half-lives. This marker will be disposed of after each use as biological hazardous material.

Figure 9:
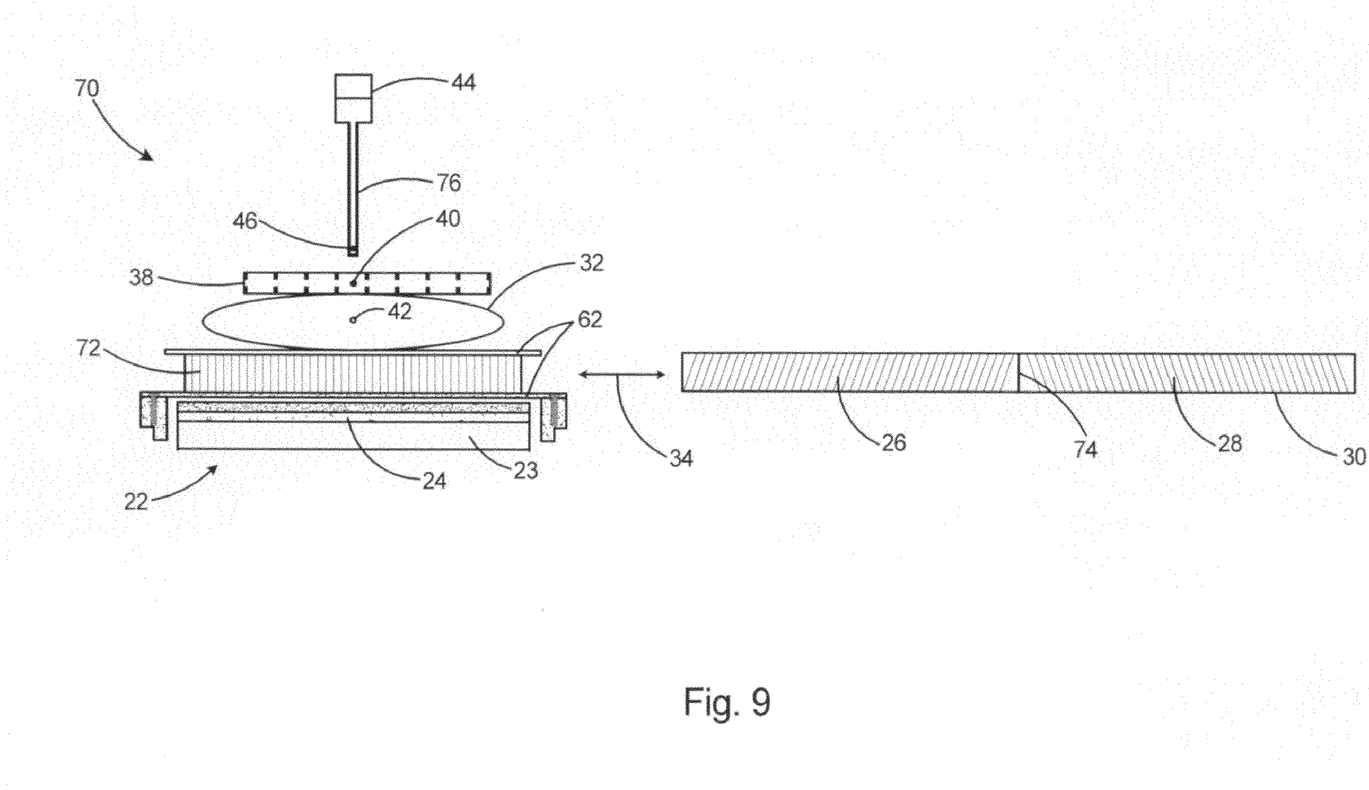
FIG. 9 is a conceptual front view of a second embodiment of a gamma guided stereotactic localization system according to the present invention including a gamma camera crystal, a stereo imaging system including a parallel hole collimator and a set of oppositely viewing slant-hole collimators, and a grid localization system with a fiducial marker source.

With reference to FIG. 9 there is shown an alternative embodiment of the gamma guided stereotactic localization system 70 that includes a parallel-hole collimator 72 and a stereo-collimator assembly 30 made from a pair of 20-degree slant-hole collimators 26 and 28. Both the parallel-hole collimator 72 and the slant-hole stereo-collimator assembly 30 slide in a cassette 62 that mounts on the top of the gamma camera 24. The parallel-hole collimator 72 is slid into the cassette 62 and used to produce a "scout" image. This image is used to determine the X and Y location of the region-of-interest 42. The slant-hole collimator assembly 30 then slides into the cassette 62. Images are then taken to determine the Z location (depth) of the suspected regions.

A region of interest can be identified in the gamma guided stereotactic localization system 70 of FIG. 9 by either of two methods. In one method, the location of the region-of-interest 42 in the images taken with the parallel-hole collimator 72 and the slant-hole collimators 30 are used to calculate the location of the suspected region. The X and Z location of the region can be determined from the following expressions:

$$X = \frac{X^L + X^R}{2} \quad (1)$$

$$Z = \frac{(X^L - X^R)}{2\tan\theta} \quad (2)$$

where $X^L$ and $X^R$ are the X locations of the region-of-interest in the left and right viewing images and $\theta$ is the slant-hole angle, which in a preferred embodiment is 20 degrees. In a second method, the location of the region-of-interest 42 is determined interactively by aligning a source, such as fiducial source 40 in FIG. 9, with the location of the region, as determined by the images from the parallel-hole collimator 72 and slant-hole collimators 30. For small isolated regions of uptake this method is preferred. For large regions or multi-focal uptake, the first method is preferred.

In order to calculate the location of the region of interest a parallel-hole collimator 72 is slid into the cassette 62 and used to produce a scout image. The scout image is used to determine the X and Y location in the plane of the detector of the region of interest. The parallel-hole collimator 72 is then removed from the cassette 62 and the slant-hole collimator assembly 30 is slid into the cassette. One or two images are then taken to determine the depth or Z location of the suspected region or regions. For small isolated regions of uptake a single image can be taken where the region is in the field-of-view of both slant-hole collimators. For large regions or multi-focal uptake, two images may be needed to determine the depth of all of the regions.

When determining the location of a region-of-interest interactively by the second method, the parallel-hole collimator 72 is used and a source 46 is positioned above the object 32 and aligned with the region to determine the location in the X and Y dimensions. This can either be a sealed source such as source 46 depicted in FIG. 9 or a drop of Tc-99m that is moved above the object 32. To determine the Z location, the slant-hole collimator assembly 30 is positioned such that the line 74 where the slant-hole sections 26 and 28 are joined is placed under the region-of-interest 42. A source 46 is placed in a vessel that can be inserted into the breast, such as the biopsy needle portion 76 of biopsy needle guide 44, and the image of the source 46 is monitored in both stereo views. The correct Z location is determined by aligning the image of the source 46 and the image of the region-of-interest 42 in the two views. A sketch of the overlap region 78 is shown in FIG. 1. The figure indicates the portion of the breast that can be seen by the left side collimator 26 and right side collimator 28 if the line 74 where the slant-hole sections are joined is placed directly under the region of interest 42.

The relationship between the height of the point source and the separation of the images of the point source created by the two halves of the slant-hole collimator pair 30 could be determined from the geometry of the stereo imaging system. The relationship between the height above the collimator assembly 30 and the separation of the images produced by the two slant-hole collimators 26 and 28 is given by:

$$h = s/2 \tan\theta - h_0 = (s-s_0)/2 \tan\theta \quad (3)$$

where h is the height above the collimator assembly (in mm), s is the separation of the two images (in mm), $\theta$ is the slant-hole angle, $h_0$ ($=s_0/2 \tan\theta$) is the height of the collimator above the gamma camera crystal 24 and $s_0$ is the separation of the two images when the source is on the surface of the collimator. The separation of the images can be determined in terms of the pixel separation by the equation:

$$s = p \cdot \text{pixel spacing} \quad (4)$$

where p is the separation in pixels and the pixel spacing for a preferred embodiment of the gamma camera is 3.2 mm/pixel. The height above the gamma camera crystal 24 can be determined from the design of the camera system. It is the sum of the size of the collimator (siz), the separation between the collimator and the camera (sep) and the depth of the crystals within the camera (dep). The total height can be determined from:

$$h_0 = \text{siz} + \text{sep} + \text{dep} = 27.2 + 5.1 + 6.2 = 38.5 \quad (5)$$

where all dimensions are in mm. Using these values, an expression for the height of the source can be determined from the separation of the images of the point sources from the following equation:

$$h = p \cdot (\text{pixel spacing}/2 \tan 20°) - (\text{siz} + \text{sep} + \text{dep})$$

Substituting the values of these parameters gives an equation of the form:

$$h = p \cdot 4.4 - 38.5 \quad (6)$$

Figure 10:
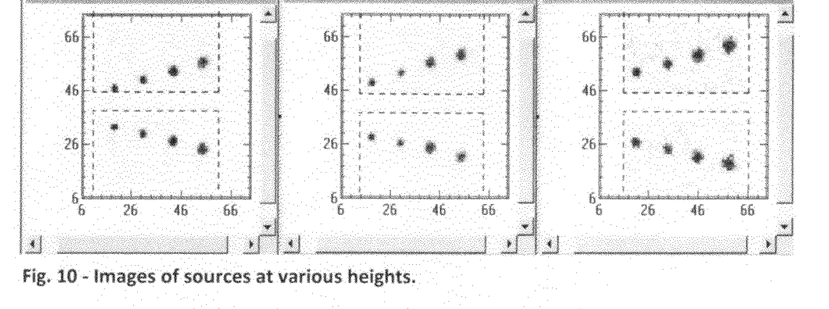
FIG. 10 is a graph depicting gamma camera images of point sources at various heights when imaged with a slant-hole collimator pair aligned such that the seam where the two collimators are joined was placed directly under the point sources.

To determine if the relationship between the height of the point source and the separation of the images of the source can be reliably determined from the relationship given in equation (6) above, measurements were made of the separation of the images of point sources are various heights and compared with the value determined from the equation. Four sources were placed on spacers of various heights and placed on the detector. Images were taken of these four sources with the slant-hole collimator pair 30 aligned such that the seam 74 where the two collimators 26 and 28 are joined was placed directly under the point sources. This was repeated three times with different sets of spacers each time. The images are shown in FIG. 10.

Figure 11:
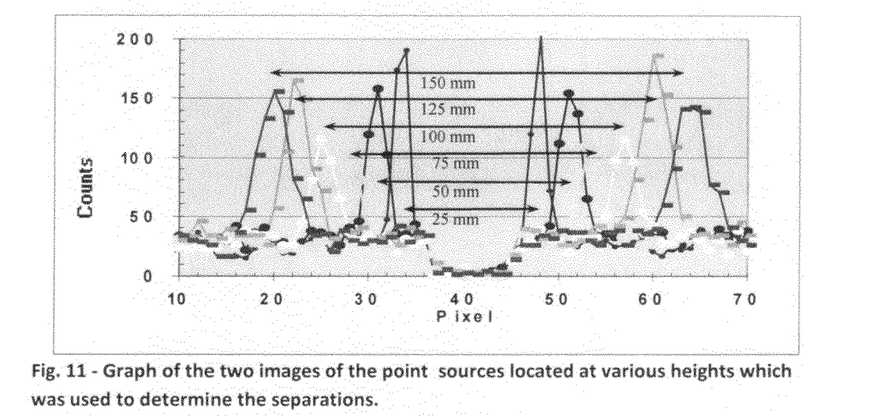
FIG. 11 is a graph depicting two images of the point sources located at various heights which was used to determine the separations of the point sources.
Figure 12:
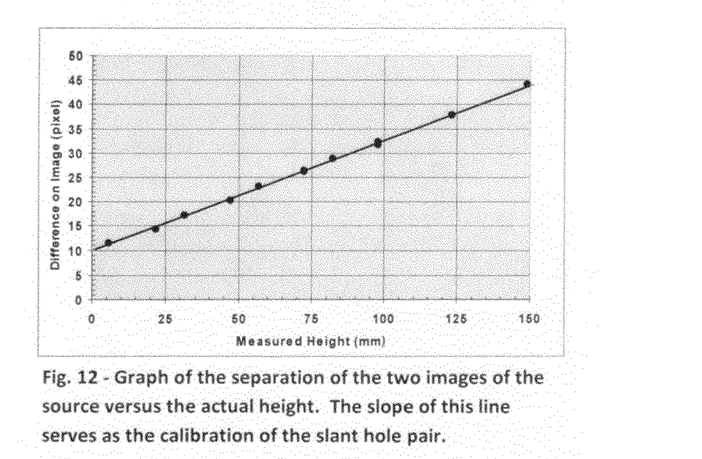
FIG. 12 is a graph of the separation of the two images of the source versus the actual height.

The images indicate that the separation of the images produced by the two halves 26 and 28 of the slant-hole collimator pair 30 scales directly with the height of the source above the collimator assembly 30. The separation of the point sources was determined for these three images. Each pair of images was projected onto the axis parallel to their separation and the peak locations were determined. Examples of these projections are given in FIG. 11. A center of gravity calculation was used to determine the peak location for each of the pairs, such that sub-pixel resolution could be achieved. The separation in these peaks determined from the center of gravity calculation was plotted versus the actual height of the source above the collimator assembly 30 in FIG. 12 to determine the relationship between the height and the separation on the image. Also plotted in FIG. 12 is equation (5), the equation used to predict the relation between the height and separation. The results plotted in FIG. 12 show that the measured relationship between the height and the separation compares well with the expected values.

Measurements were made to determine the field-of-view (FOV) that could be viewed by the two slant-hole collimators 26 and 28 simultaneously (see FIG. 1). These measurements were compared with geometric considerations to determine if the field of view could be reliably predicted. The field of view seen by both of the slant-hole collimators is determined by the slant-hole angle. This width of this field of view is given by the following expression:

$$FOV = 2 \cdot h \cdot \tan \theta, \quad (7)$$

where $2^*\tan \theta \approx 0.73$. If the separation of the sources is to be determined and a center of gravity calculation used to determine the pixel location of the sources, the blurring of the collimator must be taken into account. The blurring of the collimator with height can be approximated by a linear function and added to the expression to give a better approximation of the effective field of view of the overlap region. Assuming the width of a point source (w) increases linearly with height, the field of view would be decreased by this width. The expression for the field of view would then be expressed by:

$$FOV = 2 \cdot h \cdot \tan \theta - k \cdot h \quad (8)$$

where $w = k^*h$ and $k$ is the coefficient that describes the increase in width with height. The value of k for the preferred embodiments of the collimators 26 and 28 described herein is approximately, $k \approx 0.24$. This reduces the size of the field of view by approximately 30%.

Tests with point sources and phantoms were conducted to determine the accuracy and functionality of the sliding slant-hole collimator system. As described herein, point sources were used to determine the spatial resolution and sensitivity of the collimator system, the field-of-view of the slant-hole pair, and to demonstrate an ambiguity that exists with stereotactic imaging. Gelatin breast phantoms were used to investigate the accuracy with which a region-of-interest could be located and removed from breast tissue using the collimator system for guidance. The results indicate the successful simulated biopsies could be performed with the gamma guided stereotactic localization systems 20 and 70 of the present invention.

The spatial resolution of the gamma guided stereotactic localization systems 20 and 70 of the present invention has a large impact on the accuracy of the determination of the Z-coordinate or depth of the region-of-interest because of the angle involved in the stereo view. As can be seen from equation (2), the spatial resolution in the Z dimension is a factor of $\frac{1}{2} \tan \theta = 1.4$ times the resolution in the X dimension.

As described herein, a gamma guided stereotactic localization system consisting of a sliding slant-hole collimator arrangement can be used to produce stereo images from a compact gamma camera and to determine the three dimensional location of a region of interest. The gamma guided stereotactic localization system of the present invention has been successfully used to perform vacuum assisted biopsy procedures on gelatin breast phantoms.

Although the description above contains many specific descriptions, materials, and dimensions, these should not be construed as limiting the scope of the invention but as merely providing illustrations of some of the presently preferred embodiments of this invention. Thus the scope of the invention should be determined by the appended claims and their legal equivalents, rather than by the examples given.

What is claimed is:

1. A gamma guided stereotactic localization system comprising:
    a gamma camera;
    a cassette mounted on top of said gamma camera;
    a sliding slant-hole collimator arrangement including a set of oppositely viewing slant-hole collimators coplanar to each other and adapted to slide within said cassette, each of said collimators having parallel slant holes therein;
    said set of slant-hole collimators slideable within said cassette;
    a grid localization plate mounted above said cassette and adjustable in distance with respect to said cassette, said grid localization plate including grid openings therein;
    a biopsy needle guide including a biopsy needle positioned above said grid localization plate;
    a gamma emitting fiducial source in said grid localization plate; and
    a gamma emitting marker source in said biopsy needle;
    wherein each of said collimators is slideable and repositionable within said cassette thereby creating opposite viewing angles and stereo images from said gamma camera and enabling determination of the three dimensional location of a region of interest.

2. The gamma guided stereotactic localization system of claim 1 wherein said set of oppositely viewing slant-hole collimators includes
    a left side slant-hole collimator viewing at a 20 degree angle to the right; and
    a right side slant-hole collimator viewing at a 20 degree angle to the left.

3. The gamma guided stereotactic localization system of claim 1 wherein
    said grid localization plate includes a plurality of said grid openings arranged in rows and columns; and
    said grid localization plate includes a cavity for accepting said gamma emitting fiducial source.

4. The gamma guided stereotactic localization system of claim 1 wherein said gamma emitting fiducial source is Co-57.

5. The gamma guided stereotactic localization system of claim 1 wherein
    said gamma emitting marker source is sealed in an inner tube; and
    said inner tube is contained in an outer cannula.

6. The gamma guided stereotactic localization system of claim 1 wherein said gamma emitting marker source is a gamma-emitting isotope including
    a half-life of at least 3 months; and
    a gamma-ray energy of at least 140 keV.

7. The gamma guided stereotactic localization system of claim 6 wherein said gamma emitting isotope is selected from the group including Ce-139 and Te-123m.

8. The gamma guided stereotactic localization system of claim 1 wherein
said gamma guided stereotactic localization system includes a spatial resolution in the Z dimension; and
the spatial resolution in the Z dimension is 1.4 times the resolution in the X dimension for a set of oppositely viewing slant-hole collimators having 20 degree viewing angles.

9. The gamma guided stereotactic localization system of claim 1 wherein said set of oppositely viewing slant-hole collimators coplanar to each other are joined end to end at a seam.

10. A gamma guided stereotactic localization system for locating a region of interest in a body part and guiding equipment to the region of interest comprising:
a gamma camera;
a cassette mounted on top of said gamma camera;
a parallel hole collimator;
a sliding slant-hole collimator arrangement including a set of oppositely viewing slant-hole collimators coplanar to each other and adapted to slide within said cassette, each of said collimators having parallel slant holes therein;
a grid localization plate mounted above said cassette and adjustable in distance with respect to said cassette, said grid localization plate including grid openings therein;
a biopsy needle guide including a biopsy needle positioned above said grid localization plate;
a gamma emitting fiducial source in said grid localization plate; and
a gamma emitting marker source in said biopsy needle;
wherein said parallel hole collimator is slideable within said cassette to obtain the X and Y location of the region of interest and said set of slant-hole collimators is slideable and repositionable within said cassette to obtain the Z location of the region of interest.

11. The gamma guided stereotactic localization system of claim 10 wherein said set of oppositely viewing slant-hole collimators includes
a left side slant-hole collimator viewing at a 20 degree angle to the right; and
a right side slant-hole collimator viewing at a 20 degree angle to the left.

12. The gamma guided stereotactic localization system of claim 10 wherein
said gamma guided stereotactic localization system includes a spatial resolution in the Z dimension; and
the spatial resolution in the Z dimension is 1.4 times the resolution in the X dimension for a set of oppositely viewing slant-hole collimators having 20 degree viewing angles.

* * * * *